United States Patent [19]

Glucksman et al.

[11] Patent Number: 4,795,883
[45] Date of Patent: Jan. 3, 1989

[54] AROMA GENERATING APPARATUS AND DRIVER CIRCUIT

[75] Inventors: Dov Z. Glucksman, Brookline; Constantine D. Pezaris, Nahant, both of Mass.

[73] Assignee: Environmental Fragrance Technologies, Ltd., New York, N.Y.

[21] Appl. No.: 108,098

[22] Filed: Oct. 13, 1987

Related U.S. Application Data

[63] Continuation-in-part of Ser. No. 70,977, Jul. 8, 1987.

[51] Int. Cl.$^4$ ................................. A61L 9/03
[52] U.S. Cl. ........................... 219/272; 219/276; 219/502; 219/518; 219/492
[58] Field of Search ............... 219/271, 272, 273, 274, 219/275, 276, 502, 506, 518, 492

[56] References Cited

U.S. PATENT DOCUMENTS

| | | | |
|---|---|---|---|
| 2,660,828 | 12/1953 | Abrams | 219/272 |
| 2,758,412 | 8/1956 | Loibl | 219/273 |
| 2,784,466 | 3/1957 | Burns | 219/272 |
| 3,895,928 | 7/1975 | Moran | 219/271 |
| 4,415,797 | 11/1983 | Choustoulakis | 219/273 |
| 4,675,504 | 6/1987 | Suhajda | 219/275 |

*Primary Examiner*—E. A. Goldberg
*Assistant Examiner*—Teresa J. Walberg

[57] ABSTRACT

An aroma generating apparatus includes a driver circuit which functions as a real time lapse counter and includes a signal indicator to designate the replacement period of useful lifetime of the aroma producing cartridge. The driver circuit continuously operates between a low frequency during the off state of the resistance heating element and a high frequency during energizing of the resistance heating element. The dual frequency permits monitoring of the real time operation of the apparatus without the need of providing memory devices to accommodate inoperative periods of the apparatus.

25 Claims, 5 Drawing Sheets

AROMA GENERATING APPARATUS AND DRIVER CIRCUIT

BACKGROUND OF THE INVENTION

This application is a continuation-in-part of application Ser. No. 070,977 filed on July 8, 1987.

The present invention relates in general to an aroma generating apparatus and driver circuit therefor, and more particularly, to such an apparatus adapted for producing an aroma from a replaceable aroma emitting cartridge and to such a circuit adapted for applying an AC drive voltage over preselected time intervals to a load circuit, such as a resistance heating element of the aroma generating apparatus, and which includes a real time lapse counter and signal indicator to designate the replacement period or useful lifetime of the aroma emitting cartridge.

An aroma generating apparatus is a device adapted for long term use in generating preselected aromas from replaceable aroma producing material contained within a housing by means of an underlying heating element. One such apparatus is disclosed in Glucksman, U.S. Pat. No. 4,631,387. These aromas, such as perfumes, air fresheners, insecticide scents and the like, are sensed by the olfactory organs which are stimulated by relatively small quantities of gases or vapors in the air as low as one part per one million parts of air. The perception of smell by an individual is such, that if a given smell persists, the individual ceases to be aware of the smell for the individual makes an accommodation to the odor which is then treated as the prevailing environment. Thus, one who first enters an aromatic environment becomes immediately conscious of the odor, but the sensitivity thereto diminishes and virtually disappears if the individual remains in the environment. When, however, the individual leaves the aromatic environment and is exposed to the outside atmosphere, he quickly senses this change.

Thus, the operation of the olfactory system is such that it is highly responsive to a change in the nature or level of an aroma but is desensitized when the prevailing odor attains a steady state condition. In a room having an aroma generating apparatus in which an aromatic vapor is continuously exuded, persons in the room subjected to the vapor cease in time to become aware of the aroma, even though it is continuously being produced, thus serving no useful purpose.

There is, however, a need for a drive circuit for operating an aroma generating apparatus which functions to freshen or scent the air in a room in which the unit is placed, which unit will function to periodically discharge into the room atmosphere bursts of aromatic vapor, the non-aromatic intervals therebetween having a duration sufficient to avoid desensitizing the olfactory response of those exposed to the vapors. In Glucksman, a bimetallic element is incorporated within the driver circuit to energize and de-energize the heating element for predetermined durations to provide an aroma burst mode and an aroma maintenance mode. As to this driver circuit, it has the inherent disadvantages attributable to the mechanical-type action of the bimetallic element.

It is further known that the operation of the olfactory system in sensing the nature or level of an aroma is highly subjective. In order to maintain an efficacious level of an aroma, it is required that the aroma producing material be replaced after a predetermined cumulative interval of aroma generation or on time. This cumulative interval should correspond to real operative time, as opposed to merely being responsive to the total time in which the aroma producing material is available for aroma generation. In the absence of the ability to detect the effective depletion of the aroma producing material, such material may be replaced prematurely, even though the aroma producing material has a continued useful life or may be replaced long after the material has reached its useful life, resulting in operating periods where the aroma generator has little, if any, effectiveness. There is unknown in the prior art an aroma generating apparatus or drive circuit which is operative for detecting and signaling the user that the aroma producing material has reached the end of its useful life, vis-a-vis cumulative real time aroma generation.

SUMMARY OF THE INVENTION

It is broadly an object of the present invention to provide an aroma generating apparatus and driver circuit therefor particularly adapted for operation on an intermittent basis having predetermined on-time and off-time, which includes a real time lapse counter and signal indicator to designate the replacement period or useful life of the aroma generating material, and which avoids one or more of the foregoing disadvantages resulting from the use of the above-mentioned prior art aroma generating apparatus and driver circuits therefor and which fulfills the specific requirements of such an aroma generating apparatus and driver circuit.

In accordance with one embodiment of the present invention, there is provided an apparatus for generating an aroma from an aroma containing material, the apparatus comprising producing means operative for producing an aroma from the material, and circuit means for providing a signal in response to a time period of operation of the producing means.

In accordance with another embodiment of the present invention, there is provided an aroma generating apparatus comprising a housing, aroma containing material receivable within the housing, producing means operative for producing an aroma from the material for a time period, and reset means for resetting the time period in response to the presence of the material within the housing.

In accordance with another embodiment of the present invention, there is provided an aroma producing cartridge for use in an aroma generating apparatus, the apparatus including circuit means operative for producing an aroma from the cartridge over a time period, the cartridge comprising a first body portion containing an aroma producing material and a second body portion operatively engageable with the circuit means for resetting the time period.

BRIEF DESCRIPTION OF THE DRAWINGS

The above description, as well as further objects, features and advantages of the present invention will be more fully understood by reference to the following detailed description of the presently preferred, but nonetheless illustrative, aroma generating apparatus and driver circuit therefor when take in conjunction with the accompanying drawings, wherein:

FIG. 4 is a perspective view of an aroma producing material, in cartridge form, for generating efficacious levels of various aromas and the like;

DETAILED DESCRIPTION

Figure 1:
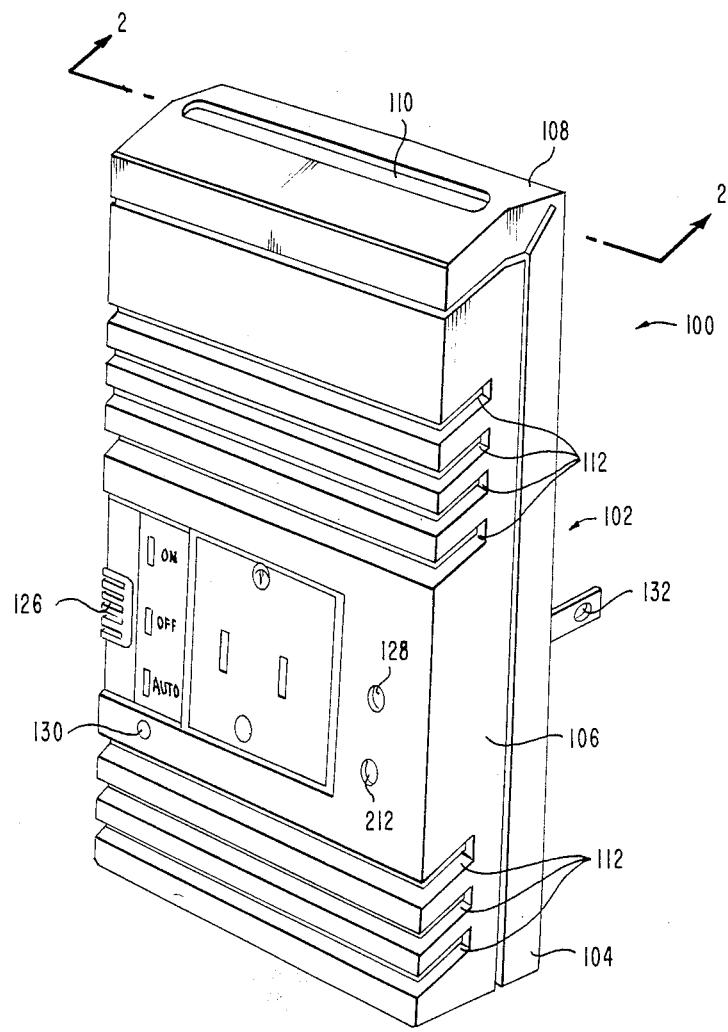
FIG. 1 is perspective view of an aroma generating apparatus adapted for discharging aromas into the surrounding atmosphere employing a driver circuit in accordance with the present invention.

Referring now to the figures, wherein like reference numerals represent like elements, there is disclosed in FIG. 1 an aroma generating apparatus 100 which includes a driver circuit constructed in accordance with one embodiment of the present invention. The apparatus 100 is more fully disclosed and described in co-pending U.S. application Ser. No. 065,840, filed on June 23, 1987, which is a Continuation-in-part of U.S. application Ser. No. 878,096, filed on June 24, 1986. The apparatus 100 is constructed from a housing 102 generally formed of molded synthetic material such as rigid and semi-rigid plastic material. The housing 102 includes a back cover 104 and a matable front cover 106 which define a hollow region therebetween. The housing 102 is provided with an open top which is closeable by means of a closure member 108 hinged to the back cover 104 and securable in a closed position. The closure member 108 is provided with a longitudinally extending opening 110 to permit liberation of aromatic vapors from the contained aroma producing material. The front cover 106 is provided with a plurality of slotted openings 112 which provide for air convection through the interior of the housing 102 and out through the opening 110 within the closure member 108.

Figure 4:
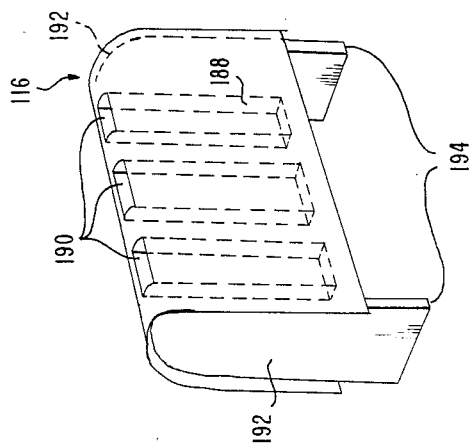
Figure 2:
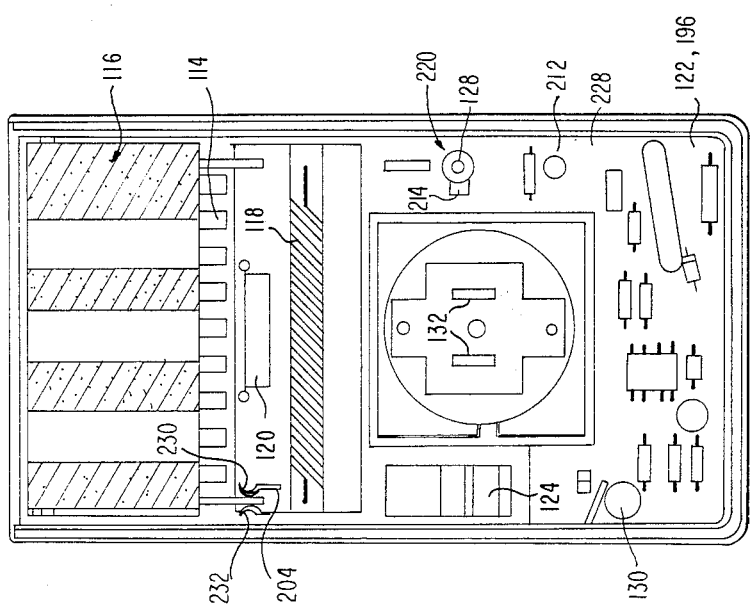
FIG. 2 is a cross-sectional view taken along the lines and arrows 2—2 in FIG. 1.

Referring now to FIG. 2, a plurality of ribs 114 extend inwardly from the back cover 104 to define a cavity thereabove. A corresponding arrangement of ribs (not shown) extend inwardly from the front cover 106. The cavity is dimensioned to receive a block of aroma producing material 116 therein through the open top of the housing 102. The aroma producing material 116, as best shown in FIG. 4, is preferably made of a porous plastic or polymer such as a porous blown polyethylene foam which is adapted to be impregnated with an oil based fragrance or other aroma producing chemicals. The aroma producing material 116, in cartridge form, can be manufactured by a variety of techniques, such as injection molding, casting and the like.

Underlying the ribs 114, there is provided a heating element assembly which includes a wound wire resistance heating element 118 and a thermostat 120. Electric power to the heating element 118 is supplied by means of an electrical driver circuit generally designated by reference numeral 122, which is supported on a printed circuit board arranged underlying the heater element assembly 118 within the housing 102. The driver circuit 122, in accordance with one embodiment, will be described hereinafter with respect to FIG. 3, and in accordance with another embodiment with respect to FIG. 6. A control switch 124 is mounted on the printed circuit board for operation of the driver circuit 122 between an off mode, on mode and automatic mode. Referring to FIG. 1, the control switch 124 is externally controlled to the desired mode by means of an external switch lever 126. An indicator, i.e., neon pilot light 128, is provided to indicate an on condition of the aroma generating apparatus 100 and a photocell 130 or the like is provided for automatic control of the driver circuit 122 in response to ambient light. Power from an external source such as 120 volts AC is supplied to the driver circuit 122 by means of a pair of male type electrical prongs 132 which are adapted for electrical connection with a conventional household socket.

Figure 3:
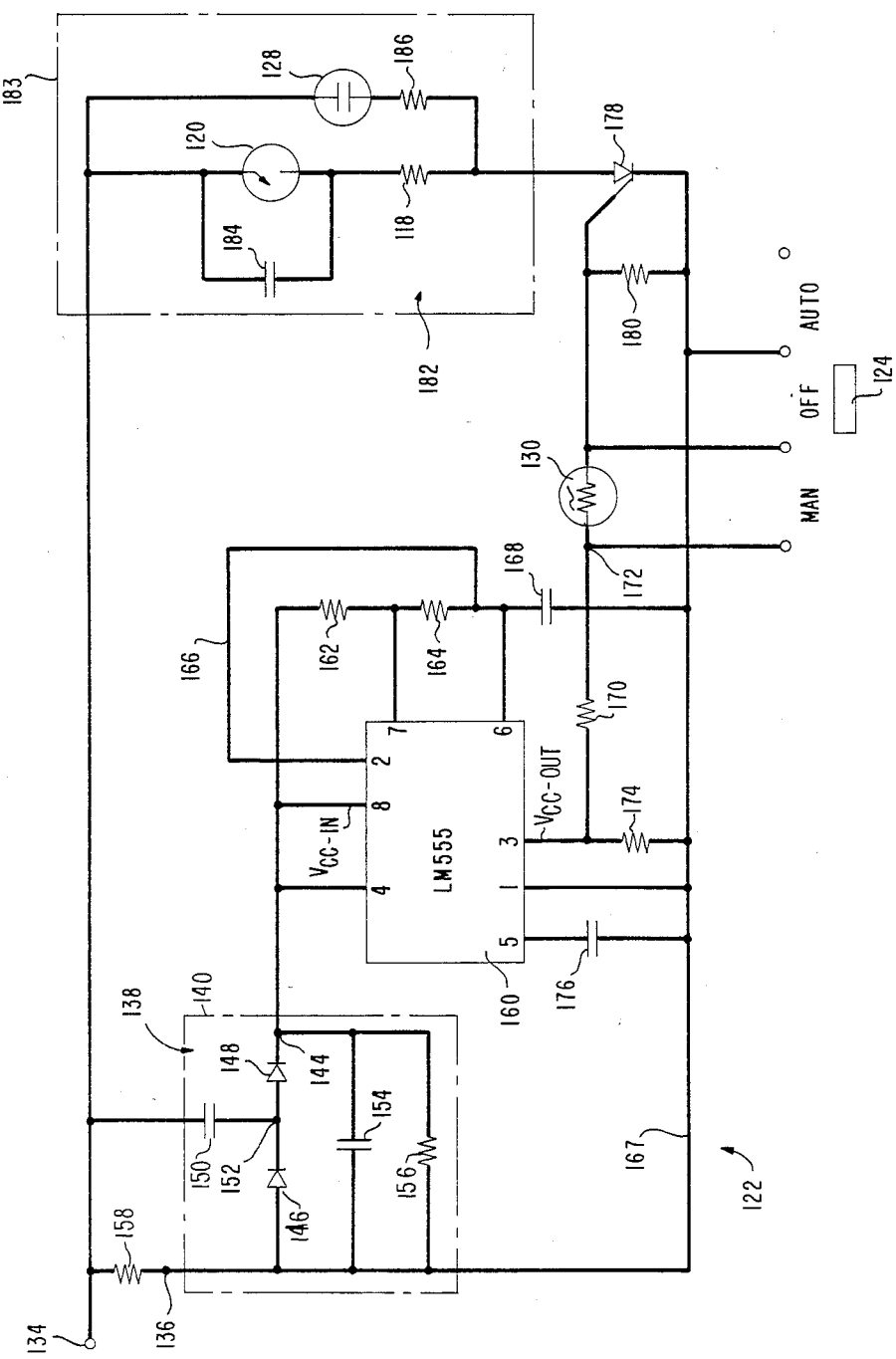
FIG. 3 is a diagram of a driver circuit constructed in accordance with one embodiment of the present invention.

Referring now to FIG. 3, there is disclosed a driver circuit 122 constructed in accordance with one embodiment of the present invention. The driver circuit 122 includes a pair of input terminals 134, 136 for receiving an input AC line voltage, for example, 115 volts, 60 cycles. A rectifier circuit 138 contained within the dashed lines 140 is connected across the input terminals 134, 136 to provide a selected DC voltage from the input AC line voltage. The rectifier circuit 138 provides an output voltage at node 144 in the range of from 9.1 to 9.3 volts DC (Vcc in). The rectifier circuit 138 includes a pair of diodes 146, 148 arranged in series, cathode to anode, between node 144 and input terminal 136. A capacitor 150 is arranged between input terminal 134 and the junction of the cathode and anode of capacitors 146, 148 at node 152. A capacitor 154 and resistor 156 are provided in parallel arrangement with respect to each other between node 144 and input terminal 136.

A resistor 158 is provided across the input terminals 134, 136. Resistor 158 functions to discharge capacitor 150 when the line input voltage is removed across input terminals 134, 136. This condition is achieved upon unplugging the aroma generating apparatus 100 from the household outlet or other source of electrical power. The discharging of capacitor 150 by means of resistor 158 is a safety feature of the driver circuit to prevent the inadvertent application of the stored charge in capacitor 150 in the event the input terminals 134, 136 are shorted by contact with an individual.

The driver circuit 122 centers around an LM 555 (Motorola) integrated circuit timer 160. The DC output voltage (Vcc in) at node 144 of the rectifier circuit 138 is applied to the input of the integrated circuit timer 160 via pin 8. The reset of the integrated timer circuit 160, pin 4, is connected to the input at pin 8 to short out the reset. This shorting causes the integrated circuit timer 160 to continuously recycle, as opposed to operating as a one shot. The input pin 8 of the integrated circuit timer 160 is connected to discharge pin 7 through a resistor 162 and further to threshold pin 6 through resistor 164. Resistors 162, 164 are connected in series such that discharge pin 7 is shorted to threshold pin 6 through resistor 164. In turn, threshold pin 6 is connected to trigger pin 2 via jumper line 166. A capacitor 168 is connected in series with resistor 164 to common line 167, i.e., ground.

The output of the integrated circuit timer 160 (Vcc out) is taken from pin 3 and applied through resistor 170 to node 172. Output pin 3 is further connected to the common line 167 through resistor 174. Ground pin 1 of the integrated timer circuit 160 is directly connected to the common line 167, while control voltage pin 5 is connected to the common line through a capacitor 176.

The output voltage of the integrated timer circuit 160 (Vcc out) is applied to the gate of a silicon controlled rectifier 178 through a photoswitch, photoresistor, phototransistor or photocell 130. The gate of the silicon controlled rectifier 178 is connected to common line 167 through resistor 180. Switch 124 is provided for operation of the driver circuit 122 in either the manual mode by shorting photocell 130, automatic mode or off mode by shorting Vcc out to common line 167.

The cathode of the silicon controlled rectifier 178 is connected to common line 167, while its anode is connected to a heater assembly 182 contained within the dashed lines 183. The heater assembly 182 includes the heating element 118 connected to the thermostat 120 which is shorted by a capacitor 184 to eliminate acoustic noise of the thermostat. A current limiting resistor 186 is arranged in series with the neon pilot light 128.

The operation of the driver circuit 122 will now be described. Upon application of 120 volts AC to input terminals 134, 136, capacitor 150 charges, raising node 152 to the corresponding voltage level. In the event of a short at the input terminals 134, 136 or at the heating element 118, capacitor 150 will maintain the desired voltage at node 152 to prevent shorting out of the driver circuit 122 and potential injury to the user. Circuit 138 operates as a diode rectifier with filter capacitor 154. During the initial positive portion of the input cycle, the diodes 146, 148 conduct and charge capacitors 150, 154 up to the peak value of the input waveform. As the input voltage decreases, the diodes go off, but node 144 is held at output voltage Vcc in by the capacitor 154 which decays through resistor 156 with a time constant (capacitor 154 x resistor 156). As the input voltage increases, the diodes 146, 148 start conducting again during which time the capacitor 154 charges back up. As the cycle repeats, the output voltage Vcc in is thus controlled to a selected value, e.g., 9.1 to 9.3 volts DC, by selecting the appropriate component values. The DC output voltage, i.e., Vcc in, from the rectifier circuit 138 is applied to input pin 8 of the integrated circuit timer 160.

The driver circuit 122 is an astable multi-vibrator charging and discharging capacitor 168 between one-third and two-thirds of Vcc in from the rectifier circuit 138. During the charging cycle, pin 3 of the integrated timer circuit 160 is maintained high at Vcc out so as to saturate the gate of the silicon controlled rectifier 178. In the case of manual operation, control switch 124 shorts out the photocell 130. Upon saturation of the gate of the silicon controlled rectifier 178, 120 volts AC from input terminals 134, 136 is applied to the heating element 118 on each positive half cycle of the 120 volts AC, 60 or 50 Hz input. The neon pilot light 128 will light and the heating element 118 will cycle in response to the thermostat 120. Because the first charging cycle immediately after applying supply voltage to input terminal 134, 136 starts from 0 volts, rather than one-third Vcc in, the first on time will be approximately 30% longer than the repeat cycling time.

The on time of the driver circuit 122 is determined by the formula 0.693×(resistor 162+resistor 164)×capacitor 168. This on time corresponds to the time of charging capacitor 168 between one-third and two-thirds Vcc in. On the other hand, the off time is determined from the formula 0.693×(resistor 164×capacitor 168). The off time corresponds to the discharge time of capacitor 168. During charging of capacitor 168, the output voltage Vcc out from pin 3 of the integrated circuit timer 160 is applied to the gate of silicon controlled rectifier 178. Thus, the gate of the silicon controlled rectifier 178 is maintained saturated during both positive and negative cycles of the AC line voltage during the entire duration of the on time of the driver circuit 122. This arrangement avoids the necessity of having to trigger the gate of the silicon controlled rectifier 178 during each positive cycle of the input line voltage. To protect the gate of the silicon controlled rectifier 178 from being burnt out due to high current or voltage, resistor 170 is provided as a current limiting resistor, while resistor 180 is provided as a voltage limiting resistor.

The above calculations for determining the on time and off time of the driver circuit 122 are based on a constant output voltage Vcc in from the rectifier circuit 138 during a full cycle of operation. In the driver circuit 122, as thus far described, voltage variations of the power line can be generally neglected. However, the internal power supply has moderate regulation, so in order to obtain reasonable time accuracy, the current of the output voltage Vcc in of the rectifier circuit 138 should be stabilized. This is achieved by the combination of resistors 170, 174 which balance the current from the integrated circuit timer 160 in the on mode when the integrated circuit timer draws less internal current. Resistor 174, when capacitor 168 is charged and pin 3 is maintained at the output voltage Vcc out, bleeds additional current off the output voltage to keep the voltage constant. This provides compensation for differences in the charging and discharging currents required of the integrated circuit timer 160. That is, the output voltage at pin 3 varies in step fashion during charging and discharging of capacitor 168, less current being required for charging than discharging.

The off time of the driver circuit 122 corresponds to the discharging time of capacitor 168. Upon capacitor 168 achieving a voltage of two-thirds the output voltage Vcc in of the rectifier circuit 138, threshold pin 6 is actuated and capacitor 168 is discharged through resistor 164 and pin 7 which is connected to ground. Resistor 162 prevents the grounding of Vcc in through pin 7 during discharge of capacitor 168. The charging of capacitor 168 through resistors 162, 174 and discharging through resistor 164 prevents the generation of a square wave form. This precludes the ability to give equal off time and equal on time, thereby providing that the discharging time will be less than the charging time.

In the automatic mode, control switch 124 is thrown to the right to place photocell 130 in line between output pin 3 of the integrated circuit timer 160 and the gate of the silicon controlled rectifier 178. The photocell 130 functions as a variable resistor in series with resistor 170. Therefore, photocell 130, resistor 170 and resistor 180 function as a voltage divider. When the photocell 130 resistance is high, the gate voltage of the silicon controlled rectifier 178 becomes too small to trigger the silicon controlled rectifier. This condition is achieved in darkness and at low light levels. On the other hand, when the photocell 130 resistance is low, the gate voltage to the silicon controlled rectifier 178 becomes sufficiently high to trigger the silicon controlled rectifier. This condition occurs under full light conditions and those conditions sufficient to provide the photocell 130 with the required resistance. Resistor 180 is varied to determine the light threshold for actuation of the photocell 130 so as to increase or decrease the sensitivity of the driver circuit 122.

Referring to FIG. 4, there is disclosed in greater detail, the aroma producing material 116 constructed in cartridge-like form. The aroma producing material 116 is integrally molded to include a main body portion 188 having a plurality of parallel arranged channels 190 extending therethrough. The channels 190 allow for the passage of heated air, via heating element 118, through the aroma producing material 116 so as to provide a chimney effect. This chimney effect enhances the liberation of aromas from the aroma producing material 116 in a uniform and efficacious manner. The ends of the body portion 188 are provided with a recessed portion 192 which extends to form a pair of depending downwardly extending, integral legs 194. The function of the legs 194 will be described hereinafter.

Figure 5:
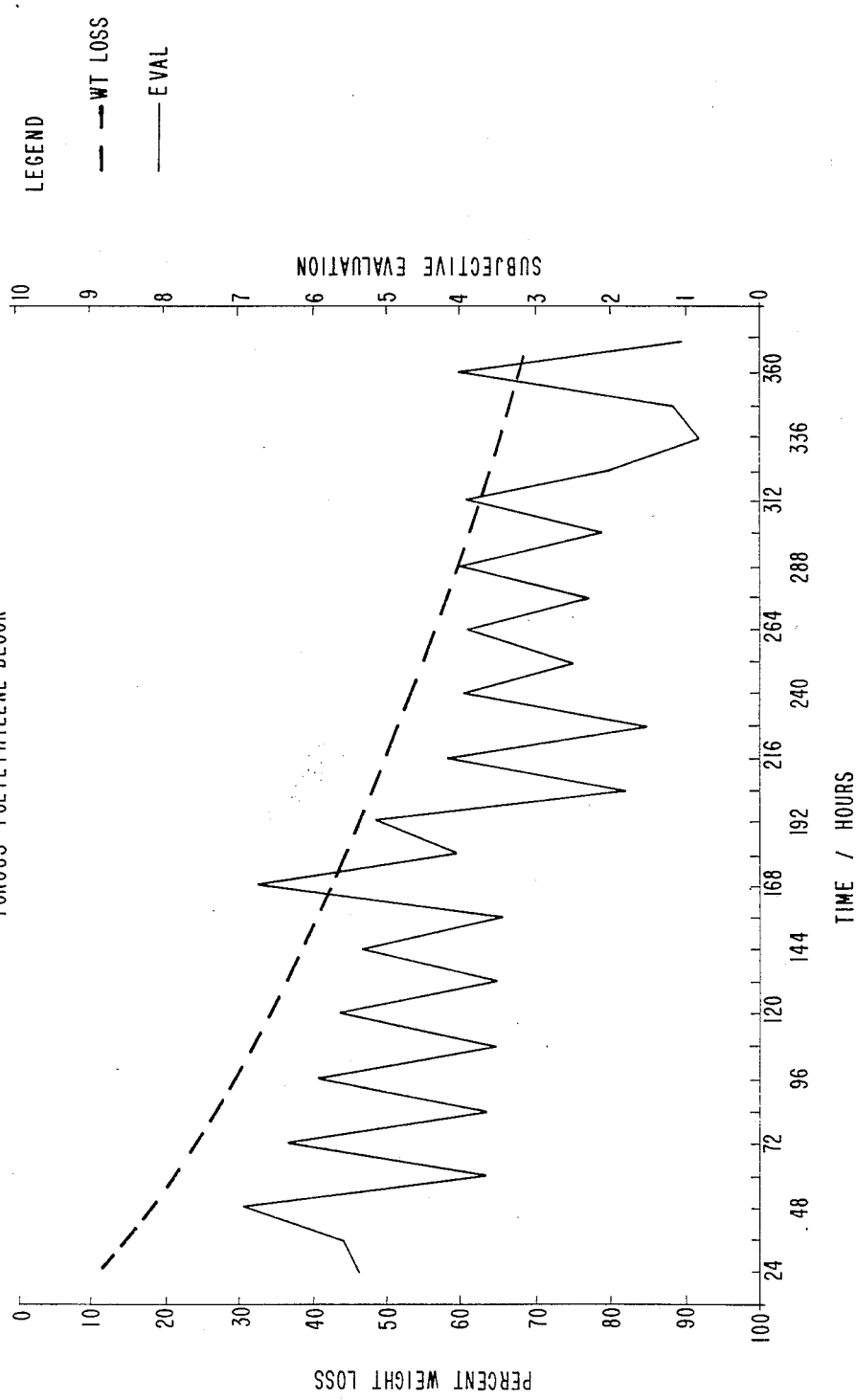
FIG. 5 is a graph showing the functional inter-relationship between the percentage weight loss of aroma producing material vs. subjective evaluation and real time operation.

Referring now to FIG. 5, there is shown a graph which illustrates the inter-relationship between percentage weight loss of the aroma producing material 116 vis-a-vis subjective evaluation of the nature and level of the produced aroma and cumulative real time operation of the aroma generating apparatus 100. As graphically shown, the weight loss of the aroma producing material 116 is a direct function of cumulative operating time of the aroma generating apparatus 100. Similarly, but to a lesser extent, there is a decrease in the subjective evaluation with respect to the nature and level of the aroma produced. To this end, it is graphically shown that after 360 hours of cumulative real time operation, the subjective evaluation is at a reasonably acceptable level, even though there is a 68% weight loss of the aroma producing material 116. From the foregoing correlation, the design of the aroma producing material 116 to have a useful real operational time life of 360 hours will result in a commercially viable product, and one which will maintain its efficacious throughout its useful life. As previously described, the useful life of the aroma producing material 116 is based upon its cumulative real time operation within the aroma generating apparatus 100, as opposed to gross installation time which would include periods of non-operation of the aroma generating apparatus. To this end, there is a need for a driver circuit for the aroma generating apparatus 100 which includes a real time lapse counter and signal indicator to designate the replacement period or useful lifetime of the aroma producing material 116.

Figure 6:
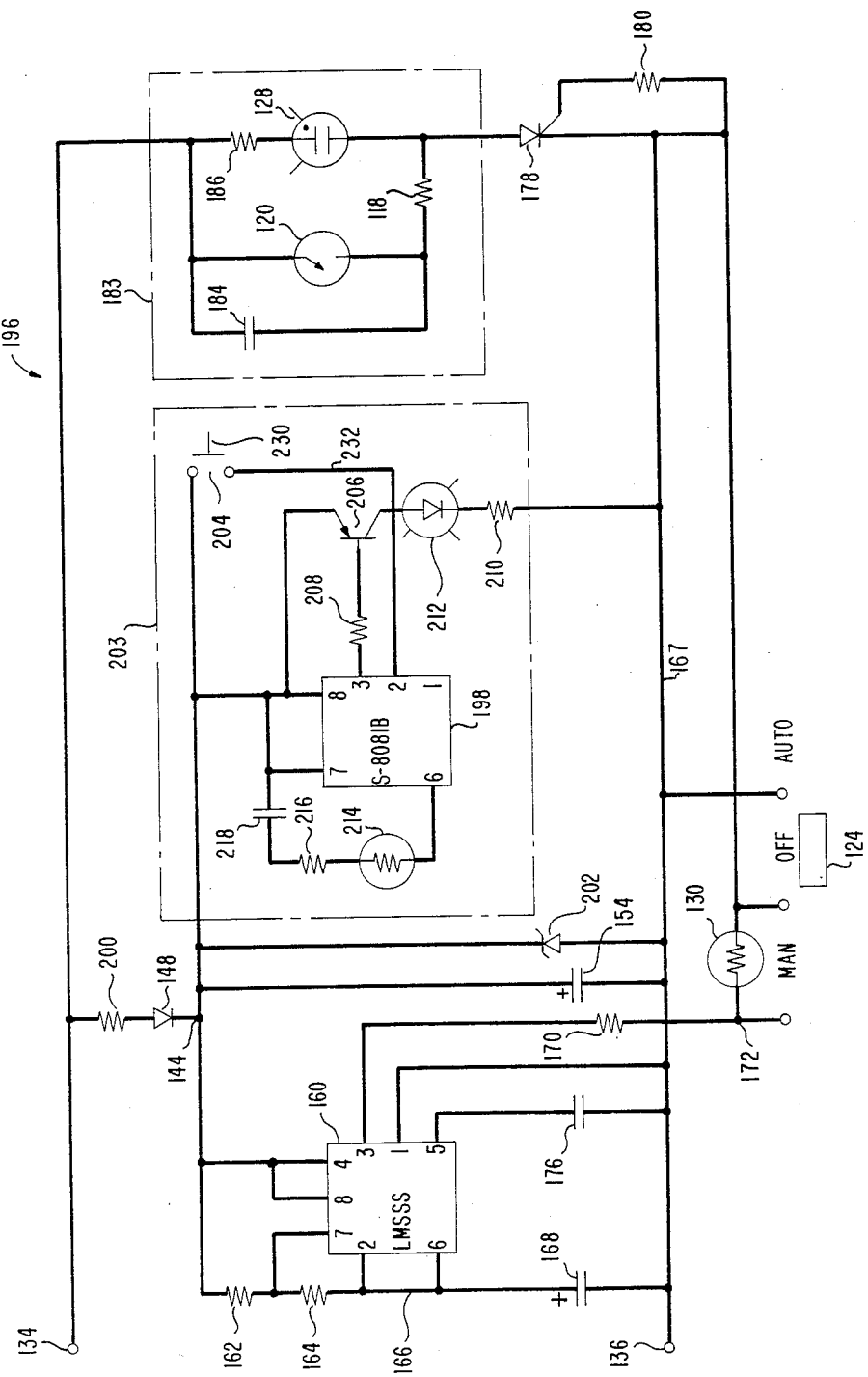
FIG. 6 is a diagram of a driver circuit constructed in accordance with another embodiment of the present invention, which driver circuit includes a real time lapse counter and signal indicator.

To this end, there is shown in FIG. 6 a driver circuit 196 in accordance with another embodiment of the present invention. The driver circuit 196 centers around the LM 555 integrated circuit timer 160 and S-8081B (Seiko) integrated circuit timer 198. The operation of the LM 555 integrated circuit timer 160 and its associated external components for applying a rectified AC drive voltage of preselected time intervals to the load circuit, i.e., heater assembly 182, is as previously described with respect to the driver circuit 122 illustrated and described with respect to FIG. 3. To this end, like components have been designated with like reference numerals, and their intended functions are the same. As such, a description of the integrated timer circuit 160 and the arrangement and operation of the its external support components will not be repeated in consideration of the foregoing description.

To this end, it is noted that resistors 156, 158 and 174, diode 146 and capacitor 150 have been omitted from the driver circuit 196. Resistor 150 has been replaced with resistor 200 arranged in series between input terminal 134 and diode 148. On the other hand, resistors 156, 174 have been replaced by Zener diode 202 arranged between node 144 and common line 167. The Zener diode 202 is provided to stabilize the voltage (Vcc out) from the integrated circuit timer 160. The driver circuit 122, as shown in FIG. 3, utilizes resistor 174 to stabilize the output voltage of the integrated circuit timer 160 resulting from the differences in on/off power requirements of the integrated circuit timer. The Zener diode 202 stabilizes the LM 555 integrated circuit timer 160 and S-8081B integrated circuit timer 198 by drawing excess current to ground, i.e., a variable bleed. However, the S-8081B integrated circuit timer 198 has its own internal power regulator, therefore, the Zener diode 202 will only have a minor effect on its regulation.

As shown in the right-hand portion of FIG. 6, there is provided a timing circuit 203 based upon the S-8081B integrated circuit timer 198 which has pin 1 connected to common line 167. Pin 2 is coupled to a reset switch 204 which in turn is connected to pin 8. Pin 8 is connected to the emitter of a transistor 206, its base being connected to pin 3 via a resistor 208 and its collector being connected to common line 167 via series arrangement of resistor 210 and indicator light emitting diode (LED) 212. Pin 6 is connected to pin 7 through a photocell 214 and resistor 216. Pin 7 is further connected to pin 8 through a capacitor 218, which in turn, are coupled to node 144.

The operation of the driver circuit 196, specifically with reference to the operation of the S-8081B integrated circuit timer 198 which functions as a real time lapse counter to provide a signal to designate the replacement period or useful lifetime of the aroma producing material 116 will now be described. The timing circuit 203 is reset by momentarily depressing reset switch 204 in the manner to be described hereinafter. When the reset switch 204 is depressed, pin 3 of the S-8081B integrated circuit timer 198 goes to a high state, shutting off transistor 206, and thereby preventing the flow of current through LED 212, which LED is now in an off state.

Figure 7:
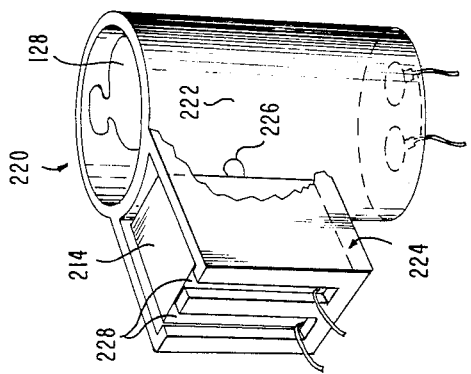
FIG. 7 is a perspective view of a housing for coupling a neon light with a photocell in accordance with the present invention.

Internally within the S-8081B integrated circuit timer 198, specifically between pins 6, 7 and 8, there is an internal RC oscillator circuit which is connected to the external timing components, namely, capacitor 218, resistor 216 and photocell 214. The output of the internal RC oscillator circuit appears at pin 3 of the integrated circuit timer 198. When the heater assembly 182 is deactivated via operation of the LM 555 integrated circuit timer 160, neon pilot light 128 remains in an off state. As the neon pilot light 128 is optically coupled to the photocell 214 via a housing 220, as shown in FIG. 7 and to be described hereinafter, the photocell acts as a high resistance element (when in its off state) so as to add to the total resistance of the time constant of the internal RC oscillator within the S-8081B integrated circuit timer 198. In accordance with the preferred embodiment, the resistance of the time constant is increased by a factor of about twenty between the on state and off state of the neon pilot light 128, vis-a-vis its optical coupling to the photocell 214. It is to be understood that other magnitudes of increasing the time constant of the internal RC oscillator circuit may be employed with the driver circuit 196 of the present invention. With the neon pilot light 128 in an off state, the internal RC oscillator circuit lowers the frequency of the S-8081B integrated circuit timer 198 by a factor of about twenty, thereby lowering the frequency at outlet pin 3 by the same amount. This timing factor may be changed by altering the values of capacitor 218, the resistor 216 or the effective resistance of the photocell 214.

As a result of the foregoing operation, the frequency of the internal RC oscillator within the S-8081B integrated circuit timer 198 is sufficiently lowered such that its cumulative real time effect during inoperative periods of the heater assembly 182 is negligible. For example, the driver circuit 196 may be designed in accordance with the preferred embodiment to require approximately 6,000 hours of inoperation before the driver circuit will indicate that the aroma producing material 116 needs replacement. This is in contrast to the driver circuit 196 indicating the need for replacement of the aroma producing material 116 after approximately 360 hours of continuous real time operation. Although the driver circuit 196 has been described via the optical coupling of neon pilot light 128 with photocell 214, it should be understood that other devices, such as a thermal switch, phototransistor and the like may be employed. In the case of a thermal switch, the thermal switch would be placed next to the heater element assembly 118.

As previously described, the neon pilot light 128 is optically coupled to the photocell 214 within the housing 220, as best shown in FIG. 7. The housing 220 is constructed of a cylindrical body portion 222 which receives the neon pilot light 128. The cylindrical body portion includes an open top which is arranged underlying a lens within the front cover 106 of the aroma generating apparatus 100. The bottom portion of the housing 220 includes two openings through which the corresponding leads of the neon pilot light 128 extend. Integrally formed with the cylindrical body portion 222 is a rectangular body portion 224. The rectangular body portion 224 is adapted to receive the photocell 214 which receives light from the neon pilot light 128 through an opening 226 provided within the cylindrical body portion 222. The leads from the photocell 214 extend through a pair of longitudinal slots 228. The housing may be integrally molded from opaque plastic material, such as polypropylene to prevent ambient light from affecting the photocell 214. As shown in FIG. 2, the housing 220 is mounted to the printed circuit board 228 provided within the aroma generating apparatus 100.

When the LM 555 integrated circuit timer 160 produces an output voltage Vcc out to the heater element assembly 118, the neon pilot light 128 turns on and emits sufficient light to turn on the optically coupled photocell 214, thereby lowering its resistance. As the resistance of the photocell 214 is lowered, the frequency of the internal RC oscillator within the S-8081B integrated circuit timer 198 is increased, for example, about twenty times as previously described. The resulting higher frequency output appears at pin 3. The S-8081B integrated circuit timer 198 includes twenty internal flip-flops. Based on the above design parameters, when the aroma generating apparatus 100 is inoperative, it will take approximately 6,000 hours to complete one internal flip-flop cycle. On the other hand, when the aroma generating apparatus 100 is operative, the higher resulting frequency will require only approximately 360 hours to complete the internal flip-flop cycle. Once the flip-flop cycle has been completed, i.e., triggering of the S-8081B integrated circuit timer 198, pin 3 will go to ground potential thereby causing current flow through LED 212 which will now light up in an on state. Capacitor 218, in addition to functioning as a timing component, acts as a filter to eliminate ripple during the operation of the photocell 214 as it operates on one-half cycle or rectified AC voltage from the silicon controlled rectifier 178.

When the LED 212 is in its on state, as a result of current flow resulting from the triggering of S-8081B integrated circuit timer 198 at the end of its cycle, the LED requires more power than available in the internal power supply of driver circuit 196. This causes Vcc out to drop below the operating voltage of the LM 555 and S-8081B integrated circuit timers 160, 198. As a result of this condition, the S-8081B integrated circuit timer 198 will stay latched in an on condition and its internal RC oscillator circuit will be inoperative. On the other hand, the LM 555 integrated circuit timer 160 will stop providing output pulses and go to an off state, thereby switching off the silicon controlled rectifier 178. In other words, once the LED 212 is activated, thereby signaling the user to replace the aroma producing material 116, the driver circuit 196 will become inoperative, thereby precluding the application of power to the heater element assembly 118.

As previously described, the timing circuit 203 is reset by momentarily depressing the reset switch 204. The reset switch 204, as more clearly shown in FIG. 2, comprises a pair of spring contacts 230, 232 which are normally biased via their spring-like construction in contact with one another. This momentary engagement of the contacts 230, 232 causes resetting of the timing circuit 203. During operation of the driver circuit 196, it is required that the contacts 230, 232 of the reset switch 204 be maintained in spaced-apart relationship to prevent premature resetting of the timing circuit 203. This is achieved by the legs 194 which depend from the main body 188 of the aroma producing material 116. When the aroma producing material 116 is inserted into the aroma generating apparatus 100, as shown in FIG. 2, one of the depending legs 194 lies between the contacts 230, 232 to maintain them in spaced-apart relationship during normal operation of the apparatus.

Removal of the aroma producing material 116 for its replacement will automatically reset the timing circuit 203 vis-a-vis, the withdrawal of its depending leg 194 from between the contacts 230, 232 of the reset switch 204. As shown in FIG. 2, the left and right-hand portion of the aroma producing material 116 is provided with a depending leg 194. This allows the aroma producing material 116 to be inserted into the aroma generating apparatus 100 irrespective of its right-left orientation. As the reset switch 204 is positioned underlying the ribs 114, it cannot accidentally be reset or engaged with one's fingers prematurely. Accordingly, for the first time, there is presented a driver circuit 196 which includes a real time lapse counter and signal indicator to designate the replacement period or useful lifetime of the aroma producing material 116.

Although the invention herein has been described with reference to particular embodiments, it is to be understood that these embodiments are merely illustrative of the principles and applications of the present invention. It is to be understood that numerous modifications may be made to the illustrative embodiments and that other arrangements may be devised without departing from the spirit and scope of the present invention as defined by the appended claims.

What is claimed is:

1. An apparatus for generating an aroma from an aroma containing material, said apparatus comprising producing means operative for intermittently producing an aroma from said material over a time period, and circuit means for providing a signal in response to the total accumulated time of intermittent operation of said producing means over said time period and substantially unresponsive to the time of intermittent inoperation of said producing means over said time period.

2. The apparatus of claim 1, wherein said circuit means includes a timing circuit having a first frequency of operation responsive to the operation of said producing means and a second frequency of operation responsive to the inoperation of said producing means.

3. The apparatus of claim 2, wherein said first frequency is substantially greater than said second frequency.

4. The apparatus of claim 1, wherein said circuit means includes reset means for resetting said time period.

5. The apparatus of claim 1, further including coupling means for coupling the operation of said circuit means responsive to the operation of said producing means.

6. The apparatus of claim 5, wherein said coupling means comprises a photocell and a light source.

7. The apparatus of claim 1, further including means for inactivating the operation of said producing means in response to expiration of said time period.

8. The apparatus of claim 1, further including an aroma containing material in cartridge-like form.

9. An aroma generating apparatus comprising a housing, aroma containing material receivable within said housing, producing means operative for producing an aroma from said material for a time period, and reset means for resetting said time period in response to the presence of said material within said housing, said housing and said aroma containing material cooperatively constructed to permit resetting of said means upon linear insertion of said material into said housing.

10. The apparatus of claim 9, wherein said producing means includes circuit means for providing a signal in response to expiration of said time period.

11. The apparatus of claim 10, wherein said circuit means includes a timing circuit having a first frequency of operation reponsive to the operation of said producing means and a second frequency of operation responsive to the inoperation of said producing means.

12. The apparatus of claim 11, wherein said first frequency is substantially greater than said second frequency.

13. The apparatus of claim 10, further including coupling means for coupling the operation of said circuit means responsive to the operation of said producing means.

14. The apparatus of claim 13, wherein said coupling means compriese a photocell and a light source.

15. The apparatus of claim 9, wherein said reset means comprises a pair of contacts separable by the presence of said aroma containing material.

16. The apparatus of claim 9, further including means for inactivating the operation of said producing means in response to the expiration of said time period.

17. An aroma producing cartridge for use in an aroma generating apparatus, said apparatus including circuit means operative for producing an aroma from said cartridge over a time period, said cartridge comprising a first body portion containing an aroma producing material and a second body portion containing aroma producing material operatively engageable with said circuit means for resetting said time period.

18. The cartridge of claim 17, wherein said first body portion includes a channel extending therethrough.

19. The cartridge of claim 17, wherein said second body portion comprises a depending leg.

20. An apparatus for generating an aroma from an aroma containing material, said apparatus comprising producing means operative for producing an aroma from said material, and circuit means for producing a signal in response to a time period of operation of said producing means, said circuit means including a timing circuit having a first frequency of operation responsive to the operation of said producing means and a second frequency of operation responsive to the inoperation of said producing means.

21. An apparatus for generating an aroma from an aroma containing material, said apparatus comprising producing means operative for producing an aroma from said material, and circuit means for providing a signal in response to a time period of operation of said producing means, and coupling means for coupling the operation of said circuit means responsive to the operation of said producing means, said coupling means comprising a photocell and a light source.

22. An aroma generating apparatus comprising a housing, aroma containing material receivable within said housing, producing means operative for producing an aroma from said material for a time period, reset means for resetting said time period in response to the presence of said material within said housing, and circuit means for producing a signal in response to expiration of said time period, said circuit means including a timing circuit having a first frequency of operation responsive to the operation of said producing means and a second frequency of operation responsive to the inoperation of said producing means.

23. An aroma generating apparatus comprising a housing, aroma containing material receivable within said housing, producing means operative for producing an aroma from said material for a time period, and reset means for resetting said time period in response to the presence of said material within said housing, circuit means for providing a signal in respones to expiration of said time period and coupling means for coupling the operation of said circuit means responsive to the operation of said producing means, said coupling means comprises a photocell and a light source.

24. An aroma generating apparatus comprising a housing, aroma containing material receivable within said housing, producing means operative for producing an aroma from said material for a time period, and reset means for resetting said time period in response to the presence of said material within said housing, said aroma containing material having a portion thereof engaging said reset means upon insertion within said housing for resetting said time period.

25. An aroma producing cartridge for use in an aroma generating apparatus having a housing, said apparatus including circuit means operative for producing an aroma from said cartridge over a time period, said cartridge comprising a first body portion containing an aroma producing material and a second body portion operatively engageable with said circuit means for resetting said time period, said housing and said cartridge cooperatively constructed to permit engagement of said second body portion with said circuit means upon linear insertion of said cartridge into said housing.

* * * * *